US00PP31180P2

(12) United States Plant Patent
Hoogkamp

(10) Patent No.: US PP31,180 P2
(45) Date of Patent: Dec. 3, 2019

(54) ***CURCUMA* PLANT NAMED 'CURSNAPA'**

(50) Latin Name: *Curcuma alismatifolia*
Varietal Denomination: Cursnapa

(71) Applicant: Timothy Johan Herman Hoogkamp, Doetinchem (NL)

(72) Inventor: Timothy Johan Herman Hoogkamp, Doetinchem (NL)

(73) Assignee: Nusilus B.V., Naaldwijk (NL)

( * ) Notice: Subject to any disclaimer, the term of this patent is extended or adjusted under 35 U.S.C. 154(b) by 0 days.

(21) Appl. No.: 15/999,867

(22) Filed: Aug. 23, 2018

(51) Int. Cl.
*A01H 5/02* (2018.01)
*A01H 6/00* (2018.01)

(52) U.S. Cl.
USPC ..... Plt./421
CPC ..... *A01H 6/00* (2018.05)

(58) Field of Classification Search
USPC ..... Plt./421
See application file for complete search history.

(56) References Cited

PUBLICATIONS

UPOV hit on *Curcuma* plant named 'Cursnapa', QZ PBR 20172087, filed Aug. 25, 2017.*

* cited by examiner

*Primary Examiner* — Anne Marie Grunberg
(74) *Attorney, Agent, or Firm* — C. A. Whealy

(57) ABSTRACT

A new and distinct cultivar of *Curcuma* plant named 'Cursnapa', characterized by its upright and columnar plant habit with outwardly arching leaves; rapid growth rate; freely clumping growth habit; leaves with dark brown-colored midveins; freely flowering habit; and large dense inflorescences with red purple-colored upper flower bracts and positioned above the foliar plane on strong and erect peduncles.

2 Drawing Sheets

Botanical designation: *Curcuma alismatifolia.*
Cultivar denomination: 'CURSNAPA'.

BACKGROUND OF THE INVENTION

The present invention relates to a new and distinct cultivar of *Curcuma* plant, botanically known as *Curcuma alismatifolia* and hereinafter referred to by the name 'Cursnapa'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* plant originated from a cross-pollination made by the Inventor in July, 2011 in Naaldwijk, The Netherlands of a proprietary selection of *Curcuma alismatifolia* identified as code number 20052099-001, not patented, as the female, or seed, parent with a proprietary selection of *Curcuma alismatifolia* identified as code number 20042080-999, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in July, 2012.

Asexual reproduction of the new *Curcuma* plant by axillary meristem culture in a controlled environment in Naaldwijk, The Netherlands since February, 2013 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cursnapa'. These characteristics in combination distinguish 'Cursnapa' as a new and distinct *Curcuma* plant:

1. Upright and columnar plant habit with outwardly arching leaves.
2. Rapid growth rate.
3. Freely clumping growth habit.
4. Leaves with dark brown-colored midveins.
5. Freely flowering habit.
6. Large dense inflorescences with red purple-colored upper flower bracts and positioned above the foliar plane on strong and erect peduncles.

Plants of the new *Curcuma* differ from plants of the female parent selection in the following characteristics:

1. Leaves of plants of the new *Curcuma* have dark brown-colored midveins whereas leaves of plants of the female parent selection have green-colored midveins.
2. Plants of the new *Curcuma* have red purple-colored upper flower bracts whereas plants of the female parent selection have pink-colored upper flower bracts.

Plants of the new *Curcuma* differ from plants of the male parent selection in the following characteristics:

1. Plants of the new *Curcuma* are more freely clumping than plants of the male parent selection.
2. Plants of the new *Curcuma* have larger inflorescences than plants of the male parent selection.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* are taller than plants of 'Curalimei'.
2. Inflorescences of plants of the new *Curcuma* are positioned higher above the foliar plane than inflorescences of plants of 'Curalimei'.
3. Plants of the new *Curcuma* have red purple-colored upper flower bracts with dark red purple-colored apices whereas plants of 'Curalimei' have dark pink-colored upper flower bracts with dark red purple-colored apices.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Cursnapa' grown in a container.

The photograph on the second sheet is a close-up view of a typical inflorescence and leaves of 'Cursnapa'.

DETAILED BOTANICAL DESCRIPTION

The aforementioned photographs and following observations and measurements describe plants grown during the spring in 17-cm containers in a glass-covered greenhouse in Naaldwijk, The Netherlands and under cultural practices typical of commercial *Curcuma* production. During the production of the plants, day temperatures ranged from 22° C. to 28° C., night temperatures ranged from 20° C. to 22° C. and light levels averaged 55 kilolux. Plants were 19 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Cursnapa'.

Parentage:

*Female, or seed, parent*.—Proprietary selection of *Curcuma alismatifolia* identified as code number 20052099-001, not patented.

*Male, or pollen, parent*.—Proprietary selection of *Curcuma alismatifolia* identified as code number 20042080-999, not patented.

Propagation:

*Type*.—By axillary meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Upright and columnar plant habit with outwardly arching leaves; freely clumping habit with about twelve basal shoots forming per plant; moderately vigorous growth habit and moderate growth rate.

*Plant height* (*soil level to top of foliar plane*).—About 70.1 cm.

*Plant height* (*soil level to top of inflorescences*).—About 75.6 cm.

*Plant diameter*.—About 63.8 cm.

Leaf description:

*Leaf arrangement*.—Alternate; simple.

*Length, fully expanded*.—About 72.3 cm.

*Width, fully expanded*.—About 5.9 cm.

*Shape*.—Narrowly oblanceolate.

*Apex*.—Acuminate.

*Base*.—Sheathing.

*Margin*.—Entire; unlobed.

*Venation*.—Parallel.

*Aspect*.—Initially upright, then outwardly arching.

*Texture and luster, upper and lower surfaces*.—Smooth, glabrous; non-rugose; matte.

*Color*.—Developing leaves, upper surface: Close to 137B to 137C. Developing leaves, lower surface: Close to between 138A and 138B. Fully expanded leaves, upper surface: Close to NN137C; midvein, close to 200C; secondary venation, close to NN137C. Fully expanded leaves, lower surface: Close to 189A; venation, close to 189A.

*Leaf sheaths*.—Length: About 22.8 cm. Width: About 1 cm. Texture and luster, upper surface: Smooth, glabrous; glossy. Texture and luster, lower surface: Smooth, glabrous; slightly glossy. Color, upper surface: Close to 144B; at the edges, close to 157D; venation, close to 143A. Color, lower surface: Close to 147D; at the edges, close to 157D; venation, close to 146D.

Inflorescence description:

*Arrangement*.—Dense and upright terminal spike inflorescences developing directly from the basal shoots with numerous showy upper flower bracts; typically each spike with about ten clusters each with about three flowers; about 90 flowers developing per plant at one time.

*Time to flower*.—In The Netherlands, plants flower from spring into autumn; flowering continuous during this period; plants begin flowering about 17 weeks after planting.

*Flower longevity*.—Flowers last about three days on the plant; flowers persistent; plants maintain good substance for about 40 days.

*Fragrance*.—Faint; sweet and somewhat spicy.

*Flower buds*.—Length: About 2.4 cm. Diameter: About 8 mm. Shape: Elliptic. Texture and luster: Smooth, glabrous; glossy. Color: Proximally, close to NN155A; mid-section, close to NN155A tinged with close to 62C; distally, close to N82A tinged with close to 83A and 83B.

*Inflorescence length*.—About 15.8 cm.

*Inflorescence diameter*.—About 9.5 cm.

*Flowers*.—Length: About 4 cm. Diameter: About 2.4 cm by 2.9 cm. Flower throat diameter: About 8 mm. Flower tube length: About 2.2 cm. Flower tube diameter: About 5 mm. Shape and arrangement:

Zygomorphic with three petals, conspicuous labellum and two lateral corolla lobes (staminodia), fused towards the base; gamosepalous calyx with three sepals.

*Labellum*.—Length: About 4.5 cm. Width: About 4.3 cm. Shape: Spatulate. Apex: Praemorse. Margins: Entire; slightly undulate. Texture and luster, upper surface: Smooth, glabrous; slightly velvety; matte. Texture and luster, lower surface: Smooth, glabrous; slightly glossy. Color: When opening and fully opened, upper surface: Close to 83B fading towards the base, close to 83C to 83D; central narrow stripe, close to 13A to 13B; venation, close to 83A; color becoming closer to 71B with development. When opening and fully opened, lower surface: Close to 83B to 83C fading towards the base, close to lighter than 83D; venation, close to N82A; color becoming closer to N74C to N74D with development.

*Lateral corolla lobes*.—Length: About 4.3 cm. Width: About 1.2 cm. Shape: Oblanceolate. Apex: Bluntly acute. Margins: Entire; slightly undulate. Texture and luster, upper surface: Smooth, glabrous; matte. Texture and luster, lower surface: Smooth, glabrous; slightly glossy. Color: When opening, upper and lower surfaces: Close to NN155D; distally tinged with close to lighter than 83D; venation, close to N155A; color does not change with development. Fully opened, upper and lower surfaces: Close to NN155D; distally tinged with close to lighter than 83D; venation, close to N155A; color does not change with development.

*Petals*.—Length, dorsal petal: About 3.9 cm. Length, lateral petals: About 4 cm. Width, dorsal petal: About 1.4 cm. Width, lateral petals: About 9 mm. Shape, dorsal petal: Oblanceolate. Shape, lateral petals: Narrowly oblanceolate. Apex, dorsal petal: Broadly acute. Apex, lateral petals: Acute. Margins, all petals: Entire; not undulate. Texture and luster, all petals, upper and lower surfaces: Smooth, glabrous; slightly glossy. Color, dorsal petal: When opening and fully opened, upper surface: Close to NN155D; distally slightly tinged with close to lighter than 83D; venation, close to NN155D; color does not change with development. When opening and fully opened, lower surface: Close to NN155D; distally slightly tinged with close to lighter than N81C; venation, close to NN155D; color does not change with development. Color, lateral petals: When opening and fully opened, upper surface: Close to NN155D; distally slightly tinged with close to lighter than N81C; venation, close to NN155D; color does not change with development. When opening and fully opened, lower surface: Close to NN155D; distally slightly tinged with close to lighter than N81C; venation, close to NN155D; color does not change with development. Color, flower throat: Close to NN155A; venation, close to NN155A. Color, flower tube: Close to NN155A; venation, close to NN155A.

*Calyx*.—Length: About 1.8 cm. Diameter: About 6 mm by 8 mm. Sepal length: About 1.8 cm. Sepal width: About 4 mm. Sepal shape: Narrowly obovate. Sepal apex: Acute. Sepal base: Lower 40% fused. Sepal texture and luster, upper and lower surfaces: Smooth, glabrous; matte. Sepal color: When opening and fully opened, upper surface: Close to NN155D; distally, close to NN78D to lighter than NN78D. When opening and fully opened, lower surface: Close to NN155D; distally, close to NN78D to lighter than NN78D.

*Flower bracts*.—Quantity: About ten upper bracts and about nine lower bracts per inflorescence. Length, upper bracts: About 8.5 cm. Width, upper bracts: About 4.3 cm. Length, lower bracts: About 4 cm. Width, upper bracts: About 4.7 cm. Shape, upper bracts: Ovate, slightly carinate. Shape, lower bracts: Broadly obovate to inverted reniform; strongly concave. Apex, upper bracts: Acute. Apex, lower bracts: Obtuse. Base, all bracts: Fused. Margin, upper bracts: Entire. Margin, lower bracts: Entire; undulate. Texture and luster, upper bracts, upper and lower surfaces: Smooth, glabrous; moderately glossy. Texture and luster, lower bracts, upper and lower surfaces: Smooth, glabrous; moderately glossy. Color, upper bracts: When opening and fully opened, upper surface: Close to 72A; distally, close to 64A; venation, similar to lamina and distally, close to N186C. When opening and fully opened, lower surface: Close to 72A; distally, close to 59B; venation, similar to lamina and distally, close to N186C. Color, lower bracts: When opening and fully opened, upper surface: Close to 144B; distally, close to N186C; venation, similar to lamina. When opening and fully opened, lower surface: Close to between 144A and 146B; distally, tinged with close to 200B; venation, similar to lamina.

*Peduncles*.—Length: About 55.8 cm. Diameter: About 9 mm. Strength: Strong. Aspect: About 5° from vertical. Texture and luster: Smooth, glabrous; slightly glossy. Color: Close to 143A; proximally, close to 144A.

*Stamens*.—Quantity: Two per flower; fused. Filament length: About 2.3 cm. Filament diameter: About 5 mm. Filament color: Close to NN155D; distally, close to N82B. Anther length: About 6 mm. Anther width: About 1 mm. Anther shape: Narrowly oblong. Anther color: Close to 155A. Pollen amount: Moderate. Pollen color: Close to 155C.

*Pistils*.—Quantity per flower: One. Pistil length: About 3.2 cm. Style length: About 3 cm. Style color: Close to NN155D. Stigma diameter: About 2 mm. Stigma shape: Cupped. Stigma color: Close to NN155D. Ovary color: Close to 154A.

*Seeds and fruits*.—To date, seed and fruit development have not been observed on plants of the new *Curcuma*.

Disease & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Cursnapa' as illustrated and described.

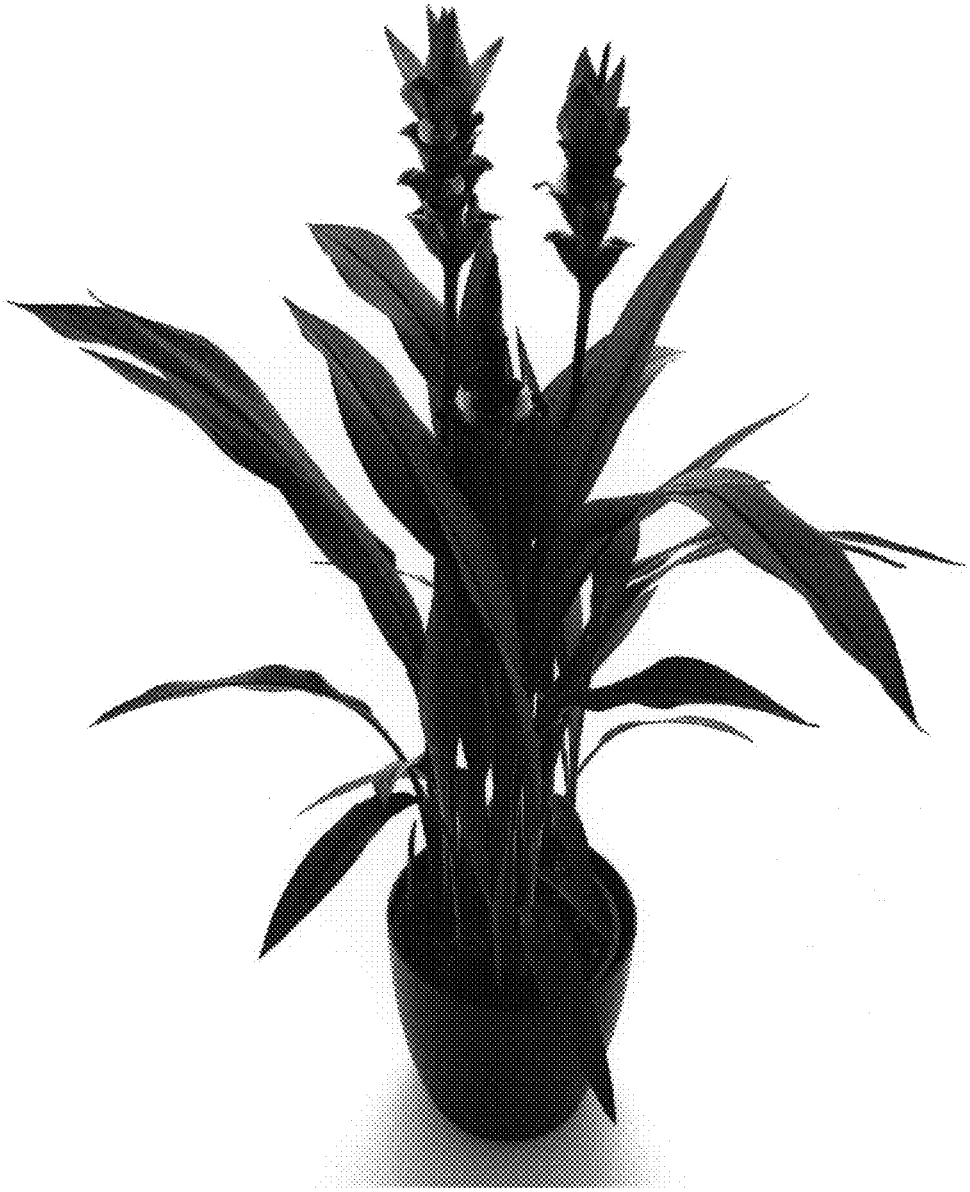

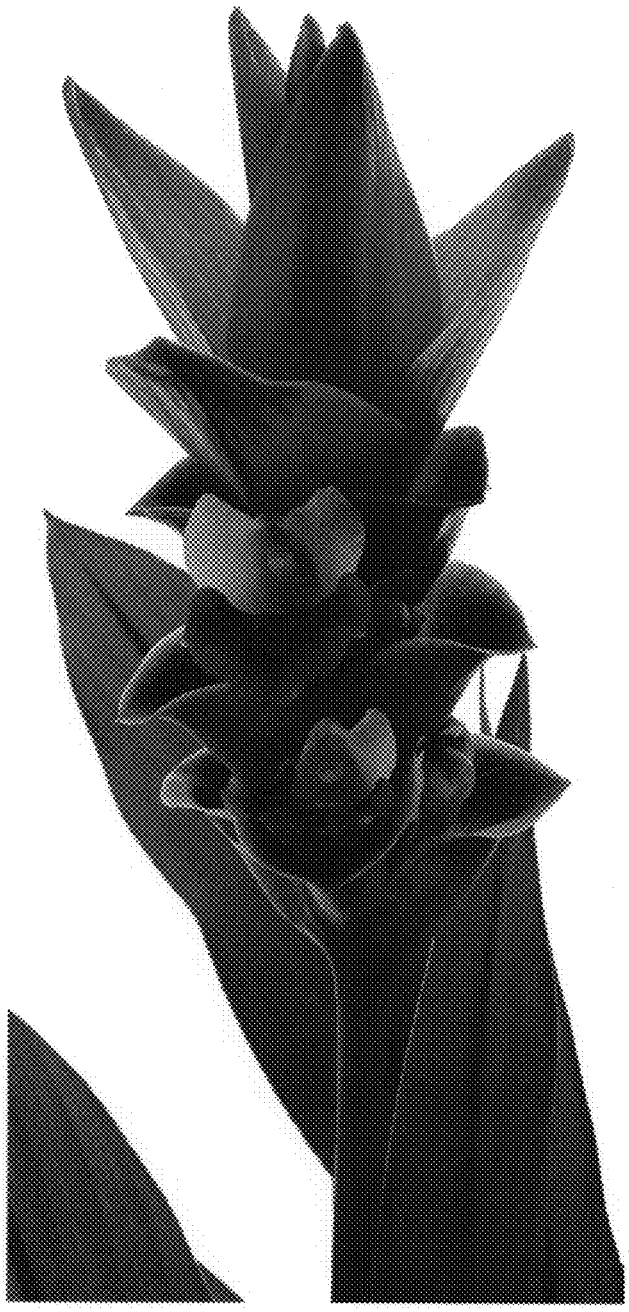

* * * * *